United States Patent
Chaligne et al.

(10) Patent No.: US 12,239,351 B2
(45) Date of Patent: Mar. 4, 2025

(54) MIXING AND DELIVERY DEVICE FOR BONE CEMENT AND ASSOCIATED METHODS

(71) Applicant: Biomet SAS, Valence (FR)

(72) Inventors: Sebastien Chaligne, Brette les Pins (FR); Julie Mottet, Chabeuil (FR); Alexis Dupuy, Sancourt (FR); Lenaic Giffard, Valence (FR)

(73) Assignee: Biomet SAS, Valence (FR)

( * ) Notice: Subject to any disclaimer, the term of this patent is extended or adjusted under 35 U.S.C. 154(b) by 499 days.

(21) Appl. No.: 17/567,561

(22) Filed: Jan. 3, 2022

(65) Prior Publication Data

US 2022/0117643 A1    Apr. 21, 2022

Related U.S. Application Data (63) Continuation of application No. 16/345,588, filed as application No. PCT/EP2017/079973 on Nov. 21, 2017, now Pat. No. 11,234,749.

(Continued)

(51) Int. Cl.
*A61B 17/88*    (2006.01)

(52) U.S. Cl.
CPC ...... *A61B 17/8833* (2013.01); *A61B 17/8802* (2013.01); *A61B 17/8822* (2013.01); *A61B 2017/8838* (2013.01)

(58) Field of Classification Search
CPC ............ A61B 17/8805; A61B 17/8808; A61B 17/8811; A61B 17/8816; A61B 17/8819;

(Continued)

(56) References Cited

U.S. PATENT DOCUMENTS 3,013,697 A * 12/1961 Gill .................. A61M 5/31596
                                                    222/129
3,417,971 A * 12/1968 Blank ................. B01F 33/5011
                                                    366/196

(Continued)

FOREIGN PATENT DOCUMENTS

CN      102395393 A      3/2012
CN      203803414 U      9/2014

(Continued)

OTHER PUBLICATIONS

"U.S. Appl. No. 16/345,588, Corrected Notice of Allowability mailed Jun. 9, 2021", 2 pgs.

(Continued)

*Primary Examiner* — Jessica Weiss
(74) *Attorney, Agent, or Firm* — SCHWEGMAN LUNDBERG & WOESSNER, P.A.

(57) ABSTRACT

Implementations described herein include a bone cement mixing and delivery device including a cylindrical container defines a chamber and has an injection passage disposed at the distal end thereof. A plug can be removably disposable in the injection passage. The mixing screw is rotatably disposable in the chamber and has a screw thread extending along an outer surface of the mixing screw as well as a return passage extending through the mixing screw from the proximal end to the distal end thereof. In a mixing mode of the device, a mixing rod engages and rotates the mixing screw about the longitudinal axis of the cylindrical container causing material disposed in the chamber to be moved distally and return to the proximal end of the chamber through the return passage of the mixing screw. In an injection mode of the device, the plug can be removed from the injection passage and an injection rod occludes the return passage of the mixing screw. The injection rod engages and (Continued)

rotates the mixing screw about the longitudinal axis moving material disposed in the chamber through the injection passage.

18 Claims, 5 Drawing Sheets

Related U.S. Application Data (60) Provisional application No. 62/425,133, filed on Nov. 22, 2016.

(58) Field of Classification Search
CPC ............ A61B 17/8822; A61B 17/8825; A61B 17/8827; A61B 17/8833; A61B 17/8836; A61B 17/8841
USPC ...................................................... 606/92–95
See application file for complete search history.

(56) References Cited

U.S. PATENT DOCUMENTS

| | | | | |
|---|---|---|---|---|
| 4,189,065 A | * | 2/1980 | Herold .................. | G01F 11/027 604/211 |
| 5,071,040 A | * | 12/1991 | Laptewicz, Jr. .... | B01F 33/5011 604/218 |
| 5,842,786 A | * | 12/1998 | Solomon ................ | B01F 31/40 366/139 |
| 5,876,116 A | * | 3/1999 | Barker ................ | B01F 33/5011 366/195 |
| 6,033,105 A | * | 3/2000 | Barker ................ | B01F 35/7511 604/93.01 |
| 9,060,826 B2 | * | 6/2015 | Coale ................. | A61B 17/8822 |
| 10,806,529 B2 | | 10/2020 | Timperley et al. | |
| 11,234,749 B2 | | 2/2022 | Chaligne et al. | |
| 2004/0030345 A1 | * | 2/2004 | Aurin ................. | A61B 17/8822 606/92 |
| 2006/0274601 A1 | | 12/2006 | Seaton, Jr. | |
| 2010/0100099 A1 | * | 4/2010 | Reilly .................. | B01F 7/0005 606/93 |
| 2016/0128752 A1 | * | 5/2016 | Greter ................. | B01F 35/7174 606/94 |
| 2019/0262051 A1 | | 8/2019 | Chaligne et al. | |

FOREIGN PATENT DOCUMENTS

| | | |
|---|---|---|
| CN | 205164641 U | 4/2016 |
| CN | 106076188 A | 11/2016 |
| CN | 109952067 A | 6/2019 |
| EP | 0445951 A2 | 9/1991 |
| WO | WO-2009158317 A1 | 12/2009 |
| WO | WO-2016068048 A1 | 5/2016 |
| WO | WO-2018095930 A1 | 5/2018 |

OTHER PUBLICATIONS

"U.S. Appl. No. 16/345,588, Final Office Action mailed Mar. 12, 2021", 15 pgs.
"U.S. Appl. No. 16/345,588, Non Final Office Action mailed Oct. 6, 2020", 16 pgs.
"U.S. Appl. No. 16/345,588, Notice of Allowance mailed Jun. 8, 2021", 5 pgs.
"U.S. Appl. No. 16/345,588, Notice of Allowance mailed Oct. 6, 2021", 5 pgs.
"U.S. Appl. No. 16/345,588, Response filed Jan. 6, 21 to Non Final Office Action mailed Oct. 6, 2020", 14 pgs.
"U.S. Appl. No. 16/345,588, Response filed May 12, 2021 to Final Office Action mailed Mar. 12, 2021", 8 pgs.
"Chinese Application Serial No. 201780070552.1, Office Action Mailed Jan. 5, 2021", (W/ English Translation), 58 pgs.
"Chinese Application Serial No. 201780070552.1, Office Action mailed Jun. 9, 2021", (W/ English Translation), 6 pgs.
"Chinese Application Serial No. 201780070552.1, Response filed Apr. 7, 2021 to Office Action Mailed Jan. 5, 2021", (W/ English Translation of Claims), 7 pgs.
"Chinese Application Serial No. 201780070552.1, Response filed Jul. 21, 2021 to Office Action mailed Jun. 9, 2021", (W/ English Translation of Claims), 11 pgs.
"European Application Serial No. 17805164.5, Response to Communication pursuant to Rules 161(1) and 162 EPC filed Jan. 22, 2020", 17 pgs.
"International Application Serial No. PCT/EP2017/079973, International Preliminary Report on Patentability mailed Jun. 6, 2019", 7 pgs.
"International Application Serial No. PCT/EP2017/079973, International Search Report mailed Mar. 2, 2018", 4 pgs.
"International Application Serial No. PCT/EP2017/079973, Written Opinion mailed Mar. 2, 2018", 5 pgs.
U.S. Appl. No. 16/345,588, filed Apr. 26, 2019, Mixing and Delivery Device for Bone Cement and Associated Methods.

* cited by examiner

1-Monomere    2-Powder

MIXING AND DELIVERY DEVICE FOR BONE CEMENT AND ASSOCIATED METHODS

FIELD

The present invention relates to a mixing and delivery device for bone cement and associated methods and systems.

BACKGROUND

Bone cement is widely used in orthopedic applications, such as to anchor components of artificial joints, and to repair or replace damaged bone tissue. Bone cement typically comprises polymethyl methacrylate (PMMA) and is conventionally provided as a two-component system comprising a powder and a liquid that require mixing prior to use. When mixing bone cement components, it is important to maximize dispersion between the liquid and powder components and to eliminate as much air as possible from the mixture in order to ensure the integrity of the bone cement.

SUMMARY

This section provides a general summary of the disclosure, and is not a comprehensive disclosure of its full scope or all of its features.

The present inventors have recognized, among other things, that a problem to be solved is providing a bone cement mixing and delivery system that does not require manual mixing and that eliminates air in the bone cement. The present disclosure can help provide a solution to these problems with a vacuumless bone cement mixing and delivery system that can involve power mixing and that can reduce or eliminate air in the bone cement.

In one example, a bone cement mixing and delivery device can comprise a cylindrical container, a plug, a mixing screw, a mixing rod, and an injection rod. The cylindrical container can include a proximal end, a distal end, a chamber extending along a longitudinal axis from the proximal end to the distal end, and an injection passage disposed at the distal end of the cylindrical chamber. The injection passage can include an inner diameter that can be less than a diameter of the chamber. The plug can be removably disposable in the injection passage. The mixing screw can be rotatably disposable in the chamber and can include a proximal end, a distal end, a screw thread extending along an outer surface of the mixing screw from proximate the proximal end to proximate the distal end of the mixing screw, and a return passage extending through the mixing screw from the proximal end to the distal end thereof.

The mixing rod can be selectively engageable with the proximal end of the mixing screw. In a mixing mode of the device, the mixing rod can engage and rotate the mixing screw about the longitudinal axis of the cylindrical container causing material disposed in the chamber to be moved distally through the chamber by the screw thread and return to the proximal end of the chamber through the return passage of the mixing screw. The injection rod can be selectively engageable with the mixing screw and extendable through the return passage to a point proximate the distal end of the mixing screw. In an injection mode of the device, the plug can be removed from the injection passage and the injection rod can occlude the return passage of the mixing screw. The injection rod can engage and rotate the mixing screw about the longitudinal axis causing material disposed in the chamber to be moved distally through the chamber and through the injection passage.

Further areas of applicability will become apparent from the description provided herein. The description and specific examples in this summary are intended for purposes of illustration only and are not intended to limit the scope of the present disclosure.

DESCRIPTION OF THE DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

The present disclosure provides for a cement mixing and delivery system that utilizes power mixing and reduces or eliminates air in the bone cement without the use of vacuum. The present disclosure further provides for a cement mixing and delivery system that can, for example and without limitation, utilize distributive mixing to uniformly disperse bone cement components and to simultaneously reduce or eliminate the presence of air within the bone cement.

In examples illustrated in FIGS. 1A-3B, a bone cement mixing and delivery device 100 can comprise a cylindrical container 102, a plug 104, a mixing screw 106, a mixing rod 108, and an injection rod 110. The cylindrical container 102 can include a proximal end 112, a distal end 114, a chamber 116 extending along a longitudinal axis 118 from the proximal end to the distal end thereof, and an injection passage 120 disposed at the distal end of the cylindrical container 102. The mixing screw 106 can be rotatably disposable in the chamber 102. The injection passage 120 can include an inner diameter that can be less than a diameter of the chamber 116. The plug 104 can be removably disposable in the injection passage 120. The device 100 can also include a lid 136 engageable with the proximal end 112 of the cylindrical container 102, the lid 136 including an aperture 138 disposed therein through which at least one of the mixing screw 106, the mixing rod 108, and the injection rod 110 extend. As discussed in detail below, the mixing rod 108 engages the top of the mixing screw 106, but leaves the central bore of the mixing 106 open to allow part of the mixing action to occur. In contrast, the injection rod 110 extends the length of the mixing screw 106 to enable ejection of the mixture via the injection passage 120.

Figure 1A:
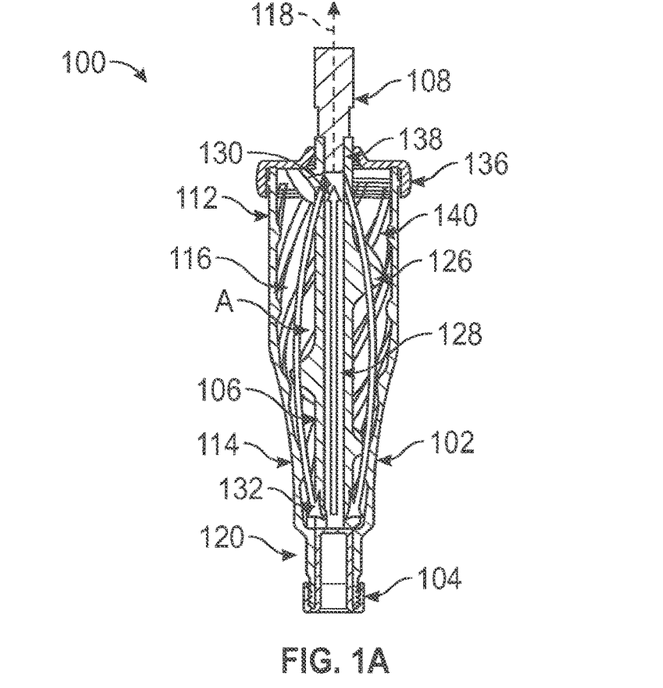
FIG. 1A illustrates a cross-sectional view of one example of a bone cement mixing and delivery device in a mixing configuration.
Figure 1B:
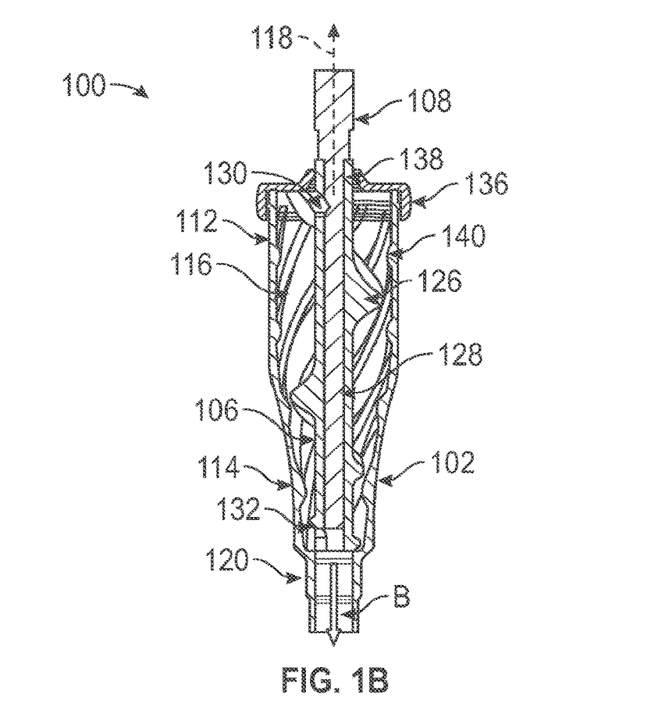
FIG. 1B illustrates a cross-sectional view of one example of a bone cement mixing and delivery device in an injection configuration.
Figure 2A:
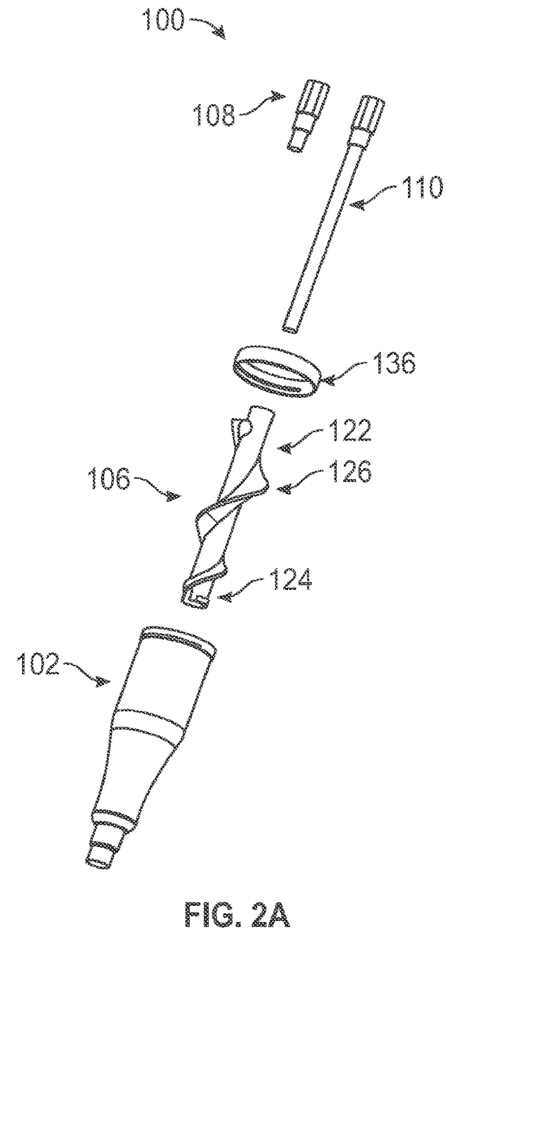
FIG. 2A illustrates a perspective exploded view of one example of a bone cement mixing and delivery device.
Figure 2B:
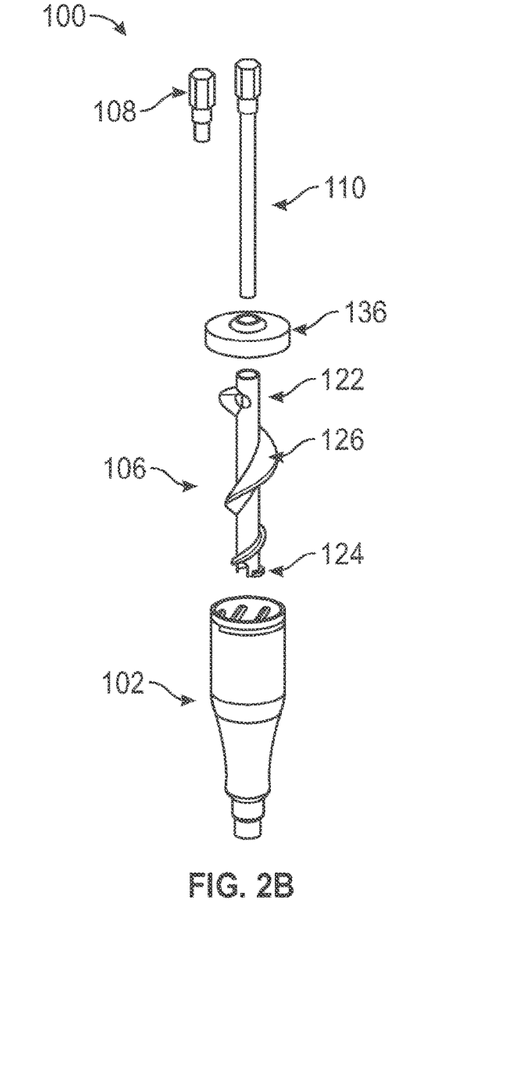
FIG. 2B illustrates a side exploded view of the bone cement mixing and delivery device of FIG. 2A.
Figures 3A, 3B:
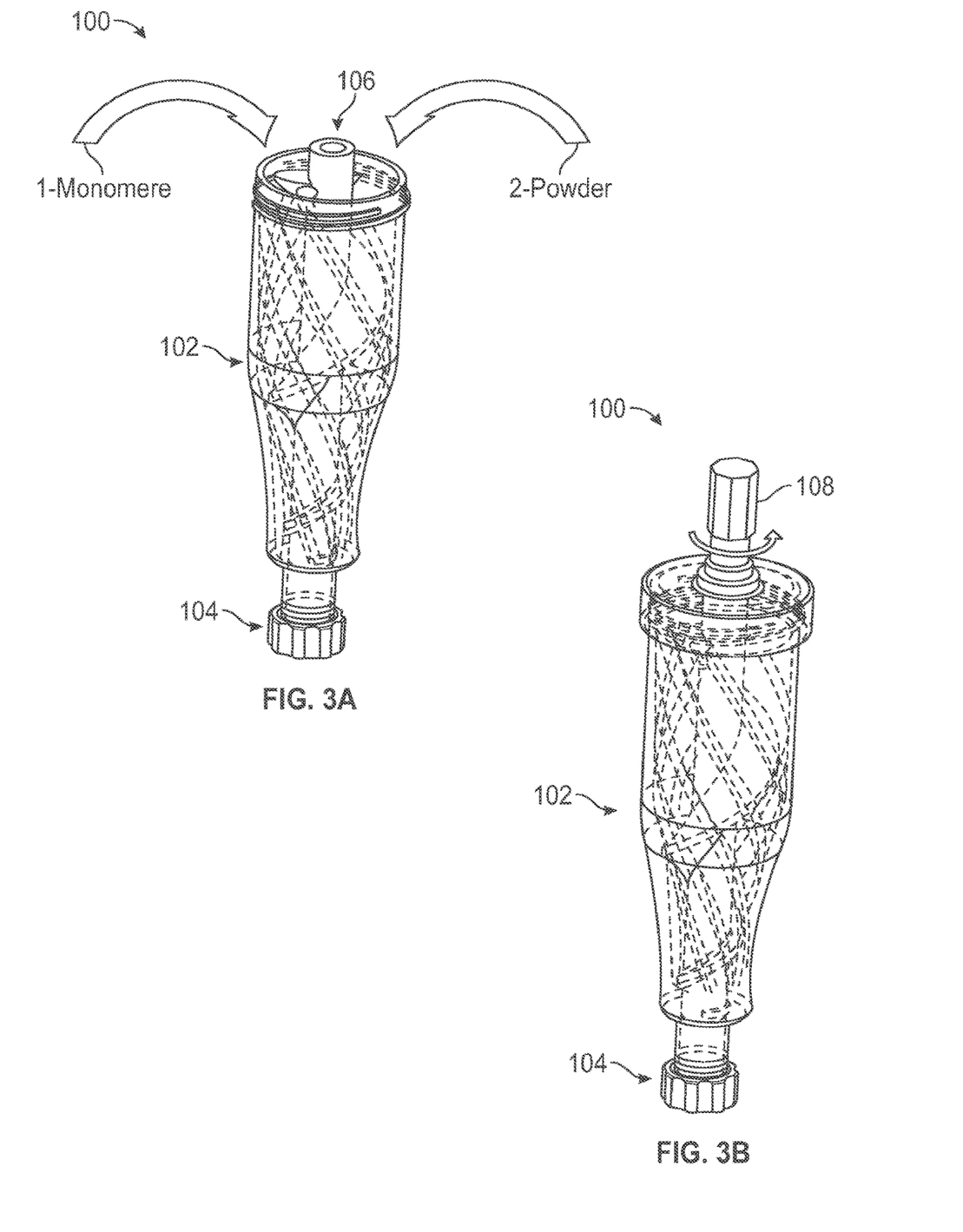
FIG. 3A illustrates a perspective view of one example of a bone cement mixing and delivery device in a loading configuration.
FIG. 3B illustrates a perspective view of one example of a bone cement mixing and delivery device in a mixing configuration.

FIGS. 2A and 2B are exploded views showing the cylindrical container 102, the mixing screw 106, the mixing rod 108, the injection rod 110, and the lid 136. The mixing screw 106 can include a proximal end 122, a distal end 124, a screw thread 126 extending along an outer surface of the mixing screw 106 from proximate the proximal end 122 to proximate the distal end 124 of the mixing screw 106, and a return passage 128 (see FIG. 1A) extending through the mixing screw 106 from the proximal end to the distal end thereof, Returning to FIGS. 1A and 1B, the mixing screw 106 can include a first void 130 disposed in and extending through a portion of a sidewall of the mixing screw 106 proximate one of the proximal end 122 and the distal end 124 of the mixing screw 106 and a second void 132 disposed in and extending through a portion of a sidewall of the mixing screw 106 proximate an opposite end of the screw from the first void 130. The first void 130 and the second void 132 are connected by the return passage 128. The mixing screw 106 can rotate in the same direction in both a mixing mode and an injection mode of the device 100. The bone cement mixing and delivery device 100 is assembled in a mixing configuration by ensuring the plug 104 is engaged in the injection passage 120, engaging the mixing screw 106 in the chamber 102, adding the bone cement components to the chamber 102, securing the lid 136, and engaging the mixing rod 108 with the proximal end 122 of the mixing screw 106. The bone cement mixing and delivery device 100 is converted from the mixing configuration to the injection configuration by removing the mixing rod 108 from the proximal end 122 of the mixing screw 106, inserting the injection rod 110 into the return passage 128 of the mixing screw so that the first void 130 and the second void 132 are occluded, and removing the plug 104 from the injection passage 120.

As illustrated in FIGS. 1A, the mixing rod 108 can be selectively engageable with the proximal end 122 of the mixing screw 106. Prior to initiating a mixing mode of the device 100, the components of the bone cement can be loaded into the cylindrical chamber 102 as further indicated in FIG. 3A. In the mixing mode of the device 100 further illustrated in FIG. 3B, the mixing rod 108 can engage and rotate the mixing screw 106 about the longitudinal axis 118 of the cylindrical container 102 causing material disposed in the chamber 116 to be moved distally through the chamber by the screw thread 126 and return to the proximal end 112 of the chamber 116 (or cylindrical container 102) through the return passage 123 of the mixing screw 106 as further described below.

As illustrated in FIG. 1B, the injection rod 110 can be selectively inserted through the proximal end 122 of the mixing screw 106 and extendable through to engage the return passage 128 to a point proximate the distal end 124 of the mixing screw 106. In an injection mode of the device 100, the plug 104 can be removed from the injection passage 120 and a solid portion of the injection rod 110 can occlude the return passage 128 of the mixing screw 106. The injection rod 110 can engage and rotate the mixing screw 106 about the longitudinal axis 118 causing material disposed in the chamber 116 to be moved distally through the chamber and through the injection passage 120 as further described below.

In one example, the distance from a thread root to a thread crest of the screw thread 126 can decrease over at least a portion of a length of the mixing screw 106 as the screw thread 126 extends from the proximal end 122 to the distal end 124 of the mixing screw 106. Additionally or alternatively, a distance between adjacent turns of the mixing thread 106 can decrease from the proximal end 122 to the distal end 124 of the mixing screw 106. The chamber 116 of the cylindrical container 102 can include a diameter that decreases distally from a first value to a second value over at least a portion of a length thereof. In one example, at least a distal portion of the cylindrical container can curve inward so as have the shape of a curved funnel. In operation, adjacent turns of the screw thread 126 can progressively compress material disposed in the chamber 116 as the screw thread 126 moves material from the proximal end 112 towards the distal end 114 of the cylindrical container 102, thereby eliminating any air in and dispersing the components of the mixture.

In another example, the chamber 116 of the cylindrical container 102 can comprise a chamber thread 140 extending along at least a portion of the length of the chamber 116. The chamber thread 140 can cooperate with the screw thread 126 to facilitate dispersion of mixture components and distal movement of material disposed in the chamber 116. In an additional or alternative example, the coefficient of friction of the surface of the mixing screw 106 can be lower than a coefficient of friction of the surface of the chamber 116. The lower coefficient of friction of the mixing screw 106 relative to the surface of the chamber 1166 can create turbulence during compression of the cement mixture by allowing the mixture to move faster at the inner diameter of the screw thread 126 and decelerating towards the outer diameter of the screw thread 126 (near the surface of the chamber 116). Such turbulence can increase the efficiency of the distributive mixing process.

In an additional or alternative example, either or both of the screw thread 126 and the chamber thread 140 can comprise a substantially triangular thread form. The substantially triangular thread form can be a triangle including at least one of a flat thread crest and a rounded transitional surface between either or both of the proximal and distal thread roots. For example and without limitation, such a thread form can reduce or eliminate any dead zones that would otherwise be present in the mixing system.

Either or both of the Mixing rod and the injection rod can be actuated by, for example and without limitation, a user, a manual crank, an electric motor, a surgical drill, a robotic arm, and the like.

The various examples of bone cement mixing and delivery devices of the present disclosure can be used to mix a liquid component and a powder component. For example and without limitation, the bone cement can comprise polymethyl methacrylate (PMMA), and the like.

Figure 4:
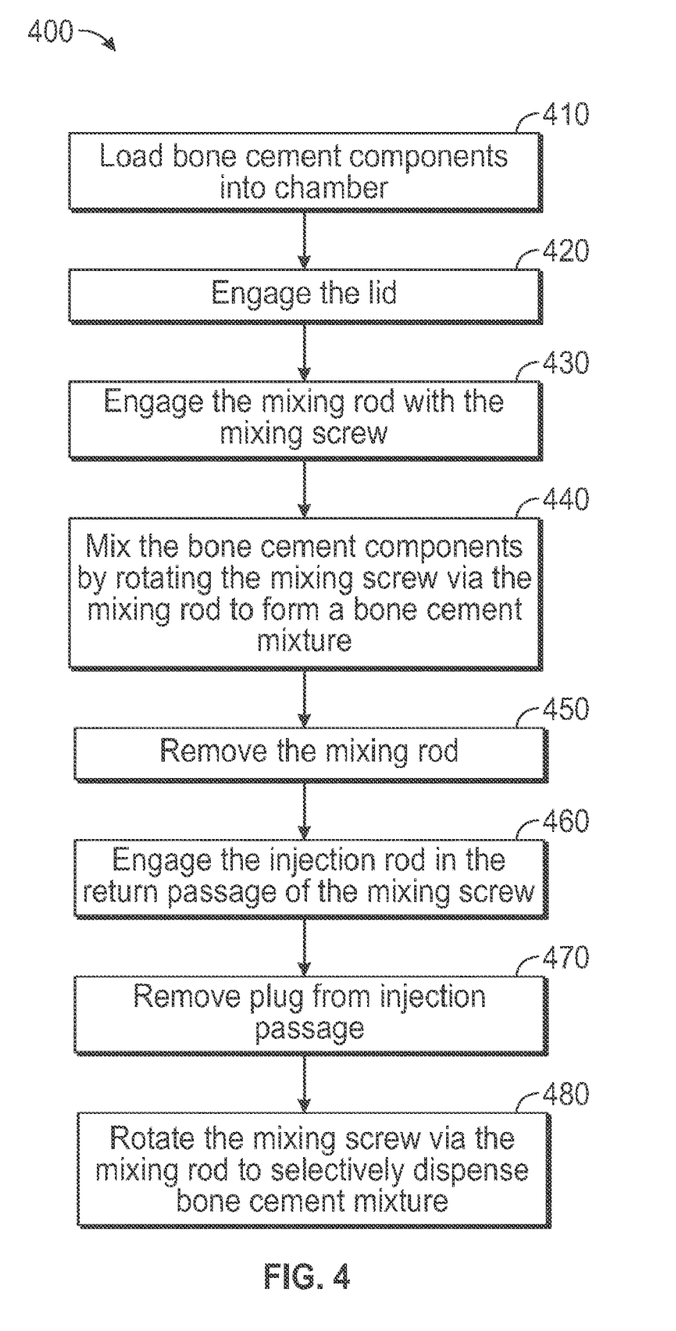
FIG. 4 illustrates an exemplary method for mixing and delivering bone cement.

In an example, as illustrated in FIG. 4, the present disclosure provides for a method 400 including steps for mixing and dispensing a bone cement mixture. The method 400 can comprise steps such as: loading bone cement components into a mixing chamber at 410, engaging a lid at 420, engaging a mixing rod with a mixing screw at 430, mixing the bone cement at 440, removing the mixing rod at 450, engaging an injection rod at 460, removing a plug at 470, and dispensing the mixture at 480.

In this example, the method 400 can begin at 410 with a user loading bone cement components (such as a monomer and a powder) into the cylindrical container 102 of a bone cement mixing and delivery device 100 through the proximal end 112 of the cylindrical container 102. In some examples, the bone cement components can include powder components comprising, for example and without limitation, one or more of pre-polymerized PMMA, PMMA or methyl methacrylate (MMA) co-polymer beads and/or amorphous powder, radio-opacifer and initiator. In some examples, the bone cement components can include liquid components comprising, for example and without limitation, one or more of an MMA monomer, stabilizer, and inhibitor. At 420, the method 400 can continue with the user engaging a lid 136 with the proximal end 112 of the cylindrical container 102 to remain the mixture components and prepare for mixing. At 430, the method 400 can continue with the user inserting a mixing rod 108 through an aperture 138 disposed in the lid 136 to engage the proximal end 122 of the mixing screw 126. At 440, the method 400 continues with the user initiating the mixing process by rotating the mixing screw 106 via the mixing rod 108 to mix the bone cement components to form a bone cement mixture. As discussed above, the interaction between the mixing screw 106 and the cylindrical container 102 through rotation of the mixing rod 108 results in a mixing process that operates to eliminate air captured in the mixture (see discussion of FIG. 5A below). At 450, the method 400 continues with the user completing the mixing process by removing the mixing rod 106.

Once the mixing process is competed, the method 400 can continue at 460 with the user preparing for dispensing the mixture by inserting an injection rod 110 through the aperture 138 and the proximal end 122 of the mixing screw 106 to engage a return passage 128 extending through the mixing screw 106 proximate the distal end 124 of the mixing screw. At 470, the method 400 continues with the user removing a plug 104 disposed in an injection passage 120 disposed at the distal end 114 of the cylindrical container 102. Removing the plug 104 will allow the mixture to be dispensed upon rotation of the injection rod 110. At 480, the method 400 can complete with the mixture being dispensed by rotation of the mixing screw 106 via the injection rod 110, which selectively dispenses bone cement mixture (see discussion of FIG. 5B below).

Figure 5A:
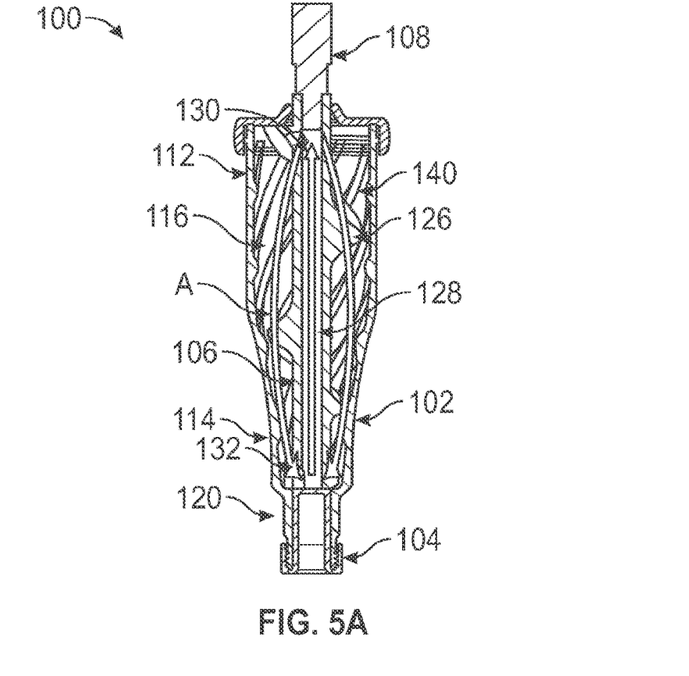
FIG. 5A illustrates an example of a bone cement mixing and delivery device in a mixing configuration.

As further illustrated in FIG. 5A, rotating the mixing screw 106 via the mixing rod 108 to mix the bone cement components to form a bone cement mixture can further comprise cyclically urging the bone cement mixture in the chamber 116 along mixing pathway A from the proximal end 112 towards the distal end 114 of the cylindrical container 102 via at least one of the screw thread 106 disposed on the mixing screw 106 and the chamber thread 140 disposed on an inner surface of the chamber 116; urging the bone cement mixture through a second void 132 disposed at the distal end 124 of the mixing screw 106, through the return passage 128, through the first void 130 into the chamber 116 proximate the proximal end 112 of the cylindrical container.

Figure 5B:
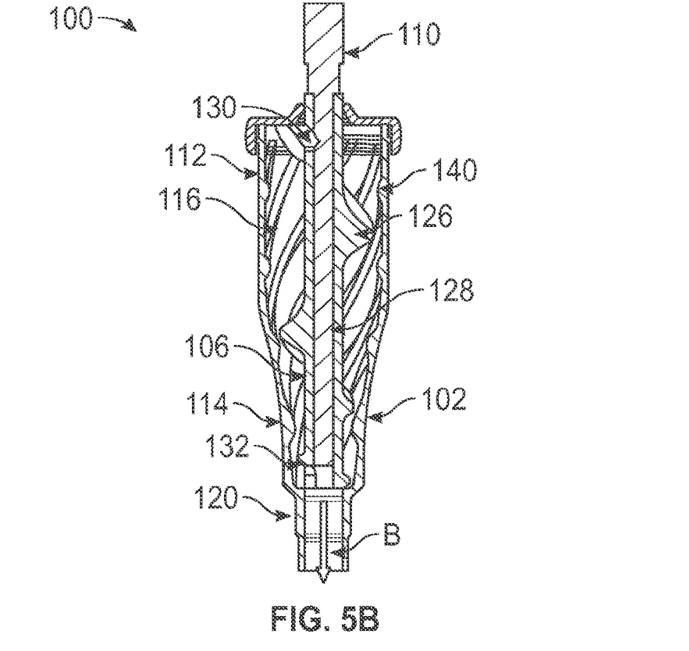
FIG. 5B illustrates an example of a bone cement mixing and delivery device in a delivery configuration.

As further illustrated in FIG. 5B, rotating the mixing screw 106 via the injection rod 110 to selectively dispense the bone cement mixture can further comprise urging the bone cement mixture in the chamber 116 along injection pathway B from the proximal end 112 towards the distal end 114 of the cylindrical container 102 and through the injection passage 120 via at least one of the screw thread 106 disposed on the mixing screw 106 and the chamber thread 140 disposed on an inner surface of the chamber 116.

VARIOUS NOTES & EXAMPLES

Example 1 is a device comprising a cylindrical container, a plug, a mixing screw, a mixing rod, and an injection rod. The cylindrical container can include a proximal end, a distal end, a chamber extending along a longitudinal axis from the proximal end to the distal end, and an injection passage disposed at the distal end of the cylindrical chamber. The injection passage can include an inner diameter that can be less than a diameter of the chamber. The plug can be removably disposable in the injection passage. The mixing screw can be rotatably disposable in the chamber and can include a proximal end, a distal end, a screw thread extending along an outer surface of the mixing screw from proximate the proximal end to proximate the distal end of the mixing screw, and a return passage extending through the mixing screw From the proximal end to the distal end thereof. The mixing rod can be selectively engageable with the proximal end of the mixing screw. In a mixing mode of the device, the mixing rod can engage and rotate the mixing screw about the longitudinal axis of the cylindrical container causing material disposed in the chamber to be moved distally through the chamber by the screw thread and return to the proximal end of the chamber through the return passage of the mixing screw. The injection rod can be selectively engageable with the mixing screw and extendable through the return passage to a point proximate the distal end of the mixing screw. In an injection mode of the device, the plug can be removed from the injection passage and the injection rod can occlude the return passage of the mixing screw. The injection rod can engage and rotate the mixing screw about the longitudinal axis causing material disposed in the chamber to be moved distally through the chamber and through the injection passage.

In Example 2, the subject matter of Example 1 optionally includes wherein the mixing screw can include a first void disposed in and extending through a portion of a sidewall of the mixing screw proximate one of the distal end and the proximal end of the screw.

In Example 3, the subject matter of Example 2 can optionally include wherein the mixing screw can include a second void disposed in and extending through a portion of a sidewall of the mixing screw proximate an opposite end of the screw from the first void.

In Example 4, the subject matter of any one or more of Examples 1-3 can optionally include a lid engageable with the proximal end of the cylindrical container, the lid including an aperture disposed therein through which at least one of the mixing screw, the mixing rod, and the injection rod extend.

In Example 5, the subject matter of any one or more of Examples 1-4 can optionally include wherein the chamber of the cylindrical container has an inner diameter that decreases distally from a first value proximate a first location towards the proximate end to a second value proximate a second location towards the distal end, the decrease in diameter occurring over at least a portion of a length of the chamber.

In Example 6, the subject matter of Example 5 optionally includes wherein the chamber can be curved inward over at least a portion of the length thereof.

In Example 7, the subject matter of any one or more of Examples 1-6 can optionally include wherein the mixing screw can rotate in a single direction in both the mixing mode and the injection mode.

In Example 8, the subject matter of any one or more of Examples 1-7 can optionally include wherein the distance from a thread root to a thread crest of the screw thread can decrease over at least a portion of a length of the mixing screw as the screw thread extends from the proximal end to the distal end of the mixing screw.

In Example 9, the subject matter of any one or more of Examples 1-8 can optionally include wherein the screw thread comprises a substantially triangular thread form.

In Example 10, the subject matter of any one or more of Examples 1-9 can optionally include wherein a distance between adjacent turns of the screw thread can decrease from the proximal end to the distal end of the mixing rod.

In Example 14, the subject matter of Example 10 can optionally include wherein adjacent turns of the screw thread progressively compress material disposed in the chamber as the screw thread moves the material from the proximal end towards the distal end of the cylindrical container.

In Example 12, the subject matter of any one or more of Examples 1-11, can optionally include wherein the cylindrical container comprises a chamber thread extending from an inner sidewall along at least a portion of the length of the chamber.

In Example 13, the subject matter of Example 12 can optionally include wherein the chamber thread can cooperate with the screw thread to facilitate distal movement of material disposed in the chamber.

In Example 14, the subject matter of any one or more of Examples 12-13 can optionally include wherein the chamber thread comprises a substantially triangular thread form.

In Example 15, the subject matter of any one or more of Examples 1-14 can optionally include a surgical motor for selectively actuating the mixing rod and the injection rod.

In Example 16, the subject matter of any one or more of Examples 1-14 can optionally include a manual crank for selectively actuating the mixing rod and the injection rod.

In Example 17, the subject matter of any one or more of Examples 1-14 can optionally include a robotic arm for selectively actuating the mixing rod and the injection rod.

In Example 18, the subject matter of any one or more of Examples 1-17 can optionally include wherein a coefficient of friction of the surface of the mixing screw can be lower than a coefficient of friction of the surface of the chamber.

Each of these non-limiting examples can stand on its own, or can be combined in various permutations or combinations with one or more of the other examples. In the examples, the terms "a" and "the" are used interchangeably, such that reference to "the plate" in a given example can refer to a plate described in a previous example that is optionally combined with the given example, or can refer to a separate tether entirely. Similarly "a plate" can refer to a newly introduced plate, or to a plate described in a previous example.

The above detailed description includes references to the accompanying drawings, which form a part of the detailed description. The drawings show, by way of illustration, specific embodiments in which the invention can be practiced. These embodiments are also referred to herein as "examples," Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be comprised within the scope of the disclosure.

What is claimed is:

1. A device, comprising:
   a mixing rod;
   an injection rod;
   a cylindrical container including a proximal end, a distal end, a chamber extending along a longitudinal axis from the proximal end to the distal end thereof, and an injection passage disposed at the distal end of the cylindrical container, the injection passage having an inner diameter that is less than a diameter of the chamber;
   a lid engageable with the proximal end of the cylindrical container;
   a mixing screw rotatably disposable in the chamber, the mixing screw including a proximal end, a distal end, a screw thread extending along an outer surface of the mixing screw from proximate the proximal end to proximate the distal end of the mixing screw, and a return passage extending through the mixing screw from the proximal end to the distal end thereof; and
   a plug removably disposable in the injection passage,
   the device being switchable from an injection mode to a mixing mode only by insertion of the plug into the injection passage,
   wherein, in the mixing mode, the mixing rod is configured to selectively engage with the proximal end of the mixing screw to rotate the mixing screw about the longitudinal axis causing material disposed in the chamber to be moved distally through the chamber by the screw thread and return to the proximal end of the chamber through the return passage of the mixing screw,
   the device being switchable from the mixing mode to the injection mode only by removal of the plug from the injection passage,
   wherein, in the injection mode of the device, the injection rod is configured to selectively engage with the proximal end of the mixing screw such that the injection rod occludes the return passage of the mixing screw and rotates the mixing screw about the longitudinal axis causing material disposed in the chamber to be moved distally through the chamber and through the injection passage.

2. The device of claim 1, wherein the mixing screw has a first void disposed in and extending through a portion of a sidewall of the mixing screw proximate one of the distal end and the proximal end of the mixing screw.

3. The device of claim 2, wherein the mixing screw has a second void disposed in and extending through a portion of the sidewall of the mixing screw proximate an opposite end of the mixing screw from the first void.

4. The device of claim 1, wherein a distance between adjacent turns of the screw thread decreases from a proximal end of the mixing rod to a distal end of the mixing rod.

5. The device of claim 1, wherein the lid includes an aperture disposed therein through which the mixing screw extends.

6. The device of claim 1, wherein the diameter of the chamber of the cylindrical container decreases distally from a first value proximate a first location towards the proximal end to a second value proximate a second location towards the distal end, the decrease in diameter occurring over at least a portion of a length of the chamber.

7. The device of claim 6, wherein an inner sidewall of the chamber is curved inward over at least a portion of the length thereof.

8. The device of claim 1, wherein the mixing screw is configured to rotate in a single direction in both the mixing mode and the injection mode.

9. The device of claim 1, wherein a distance from a thread root to a thread crest of the screw thread decreases over at least a portion of a length of the mixing screw as the screw thread extends from the proximal end to the distal end of the mixing screw.

10. The device of claim 1, wherein the screw thread comprises a substantially triangular thread form.

11. The device of claim 1, wherein adjacent turns of the screw thread progressively compress material disposed in the chamber as the screw thread moves the material from the proximal end towards the distal end of the cylindrical container.

12. The device of claim 1, wherein:
the cylindrical container comprises a chamber thread extending from an inner sidewall along at least a portion of a length of the chamber; and
the chamber thread cooperates with the screw thread to facilitate distal movement of material disposed in the chamber.

13. The device of claim 12, wherein the chamber thread comprises a substantially triangular thread form.

14. The device of claim 1, wherein a coefficient of friction of the outer surface of the mixing screw is lower than a coefficient of friction of a surface of the chamber.

15. A method for using a device according to claim 1, the method comprising:
loading bone cement components into the chamber;
and switching the device from an injection mode to a mixing mode by inserting the plug into the injection passage.

16. The method of claim 15, further comprising:
engaging the proximal end of the mixing screw with a mixing rod; and
rotating, with the mixing rod, the mixing screw about the longitudinal axis causing material disposed in the chamber to be moved distally through the chamber by the screw thread and return to the proximal end of the chamber through the return passage of the mixing screw.

17. A method for using a device according to claim 1, the method comprising:
loading bone cement components into the chamber;
and switching the device from a mixing mode to an injection mode by removing the plug from the injection passage.

18. The method of claim 17, further comprising:
engaging the proximal end of the mixing screw with an injection rod;
occluding the return passage of the mixing screw with the injection rod; and
rotating, with the injection rod, the mixing screw about the longitudinal axis causing material disposed in the chamber to be moved distally through the chamber and through an injection port of the device.

* * * * *